United States Patent
Kehoe

(10) Patent No.: US 8,951,578 B2
(45) Date of Patent: Feb. 10, 2015

(54) REBOUND HOOF PACK

(76) Inventor: Ashley Kehoe, Purcellville, VA (US)

( * ) Notice: Subject to any disclaimer, the term of this patent is extended or adjusted under 35 U.S.C. 154(b) by 0 days.

(21) Appl. No.: 13/317,190

(22) Filed: Nov. 16, 2011

(65) Prior Publication Data

US 2013/0122115 A1    May 16, 2013

(51) Int. Cl.
  *A61K 9/00*   (2006.01)
  *A01N 59/08*  (2006.01)
  *A61K 33/18*  (2006.01)
  *A61K 36/28*  (2006.01)

(52) U.S. Cl.
  CPC .................. *A61K 33/18* (2013.01); *A61K 36/28* (2013.01); *A61K 9/0014* (2013.01)
  USPC ........................................................ 424/667

(58) Field of Classification Search
  None
  See application file for complete search history.

(56) References Cited

U.S. PATENT DOCUMENTS

| | | | |
|---|---|---|---|
| 5,147,651 A * | 9/1992 | Hobson et al. | 424/443 |
| 5,464,610 A * | 11/1995 | Hayes et al. | 424/61 |
| 5,599,561 A * | 2/1997 | Gonzalez, Jr. | 424/670 |
| 5,780,064 A * | 7/1998 | Meisters et al. | 424/616 |
| 6,264,927 B1 * | 7/2001 | Monahan | 424/61 |
| 7,332,151 B2 * | 2/2008 | Yoder | 424/61 |
| 2002/0114730 A1 * | 8/2002 | Jazzar | 422/28 |
| 2004/0076614 A1 * | 4/2004 | Schur | 424/93.4 |
| 2008/0156503 A1 * | 7/2008 | McSherry | 168/2 |
| 2008/0260697 A1 * | 10/2008 | Murthy et al. | 424/93.6 |
| 2010/0316737 A1 * | 12/2010 | Farrington et al. | 424/725 |

OTHER PUBLICATIONS

Bardonescchi & Bragulla—DE 102005044554 as abstract # 2008-K55948 by WPIX.—abstract of Foam for Hoof Treatment of Animal in Farming—DE 102005044554—Mar. 29, 2007.*
Markel et al—Vetu abstract # 1985-63852. abstract of Use of Cancellous Bone Grarft in Tretment of Navicular Bone Osteomyelitis in a Foal.*
Kaneps—Vetu Abstract # 1996-61785. abstract of Orthopedic Conditions of Small Ruminants.*

* cited by examiner

*Primary Examiner* — Robert A Wax
*Assistant Examiner* — Olga V Tcherkasskaya
(74) *Attorney, Agent, or Firm* — Whitham Curtis Christofferson & Cook, PC

(57) ABSTRACT

A compound of all natural ingredients allows for treatment of infected, inflamed, and sore hooves without the need for wrapping the hoof with a diaper or vet wrap as is conventional. The compound is packable into the bottom of a hoof. A sugar base allows the compound to stick to the underside of a hoof and remain applied without the wrap. Epsom salts and iodine provide antiseptic and antimicrobial properties, and pine tar provides moisture balance within the hoof in addition to supplementing the stickiness of the compound. Applied compound may be covered with a piece of paper or cloth.

6 Claims, No Drawings

REBOUND HOOF PACK

FIELD OF THE INVENTION

The invention generally relates to the treatment of equine hooves, and, more particularly, to treatment products which stick to a hoof without a wrapping.

BACKGROUND

Working, competing, and pleasure horses are all susceptible to sore feet. Concussion and trauma to the hoof structures can leave the hooves bruised and sore. Sore feet can severely decrease the health and performance of a horse. Farriers and vets have recommended using an Epsom salt and iodine mixture, which must be placed in a diaper and duct taped to the horses hoof. The hoof soaks for a while, then the diaper, mixture, and wrapping must be removed. This process is time consuming and inconvenient. Horse hooves are also susceptible to fungus.

SUMMARY

Rebound Hoof Pack is the only product that combines all the ingredients necessary to relieve hoof inflammation, sticks to the hoof without a wrapping, and will not harm the horse's skin or test in competitions.

Rebound Hoof Pack combines all these ingredients in a super sticky mixture that sticks to the underside of the horse's hoof and stays in place without wrapping—this saves a lot of time. Its all natural ingredients ensure that competition horses will not Test for any banned substances, and the improved hoof health enables the horse to return to peak form more quickly.

There is no other product that combines all these needed ingredients together in a super sticky mixture that stays in the hoof without needing to be wrapped. Some products treat hoof health without the Epsom salts and iodine for treating inflammation and infection, while others contain ingredients like turpentine that can burn a horse's skin.

Currently, horse owners have to use salt and iodine mixed together and held onto the bottom of the horses hoof with a diaper, vet wrap and duct tape. Rebound was formulated to stick to the bottom of the horse's foot without having to wrap it with duct tape.

There is one other soreness relieving hoof pack available. There are several problems with it, which Rebound solves.

The biggest problem with all current products is that they must be wrapped onto the horses hoof to stay in place. Wrapping the foot costs time and money. Rebound is formulated to stick to the bottom of the horse's hoof, and stay in place without needing to be wrapped.

The current products do not disclose the ingredients, which poses a problem for racing and competition horses that are drug tested. The undisclosed ingredients put these horses in danger of disqualification.

Other products can also blister the horse's skin and burn the hair off the horse's heel area, leaving many dissatisfied customers. Rebound's natural ingredients will not irritate the horse's skin.

DETAILED DESCRIPTION

Rebound Hoof Pack is a compound formulated to reduce equine hoof soreness. It is a sugar-wax based compound that combines a number of proven natural ingredients targeted at relieving soreness, thereby enabling horses to comfortably and effectively practice and compete. Rebound Hoof Pack innovates the time-consuming chore of wrapping a diaper filled with Epsom salts around the hoof of the horse. Once applied to the bottom of the horses hoof, a piece of paper or cloth should be applied to the sticky side, to prevent the packing from sticking to the ground.

Rebound Hoof Pack is an all-natural product with ingredients that also keep the correct moisture balance within the hoof, promote new hoof growth, and treat bacterial and fungal hoof diseases. The salt can be overly drying, so the addition of Pine Tar keeps the correct moisture balance within the hoof, as well as adding to the stickiness of the hoof pack. The sugar-wax base is essential, for it is very sticky, all-natural, and treats bacterial and fungal hoof diseases. The addition of Epsom salts and arnica provide anti-inflammatory properties that can be absorbed into the hoof, and held together with the sugar-wax and pine-tar base. Both sugar and iodine have antiseptic and antimicrobial properties, keeping the hooves from developing, as well as treating: white line disease, seedy toe, abscesses and other bacterial and fungal based hoof diseases. Rebound Hoof Pack was formulated with the guidance of top equine veterinarians and farriers.

Ingredients include, but are not limited to:
- Epsom salt (magnesium sulfate): fine crystal
- Sugar: pure cane
- 100% lemon juice: concentrate is acceptable
- 100% pure pine tar: never mixed or cut with anything else. The thicker the better.
- Iodine: 7% concentration preferred, 2.5% tincture is acceptable. Several different brands have worked successfully.
- Arnica Montana 30×
- Leather Shavings/Sandings: finely shredded Ingredient Purposes:
- Sugar-Wax: creates a super sticky, all natural base
- Epsom salts: to draw out heat and inflammation from hoof trauma
- Iodine (active): antiseptic, anti-microbial, anti-fungal
- Pine Tar: to help ensure correct moisture balance/promote hoof growth, antiseptic
- Arnica: anti-inflammatory
- Leather scraps: improves texture Manufacturing Process:
Instructions to make approx. 3.5 lb's of Rebound Hoof Pack. Measurements are approximate.
1. Mix 3 cups Epsom salt with 1 tablespoon iodine in a separate bowl. Set aside.
2. Mix 4 cups sugar, 1 crushed 30× Arnica tablet, ¼ cup water, ¼ cup lemon juice in a large pan.
   2a. Heat on stove to 260 degrees and verify temperature with candy thermometer.
   2b. Brown sugar mix to point of slight burn which creates for a harder compound when cooled. Substance should be a dark caramel color.
3. Set heat to very low. Add 3 tablespoons pure pine tar to sugar mix, stir in slowly.
4. Stir in Epsom salt/iodine mixture until all is incorporated, stirring and allowing the salt to partially dissolve.
5. Stir in ⅓ cup leather shreddings.
6. When compound reaches a pudding-like texture pour into containers.
   6a. Use a scraper to get all the mixture out of the pot or vat.
7. Allow mixture to cool to room temperature in jars with no lid, then put lids on.

Application Directions:

Jars may be kept at room temperature and have an extensive shelf life. Rubber gloves are highly suggested in the application process given the "sticky" nature of the compound. Clean the bottom of the hoof and brush dirt out to ensure maximum absorption. Using a latex glove, scoop out a generous amount from the jar and apply firmly to all structures of the bottom of the hoof, packing well into crevices. Cover the bottom of the hoof with provided paper or cloth. No wrapping needed if in stall, but recommended if turned out in a field.

The invention claimed is:

1. A method for treatment or relief of an infection, soreness, or inflammation of a hoof of a horse, comprising the steps of:
   identifying a horse having infection, soreness or inflammation of a hoof; and
   applying an adhesive composition to a bottom of said hoof,
      said adhesive composition comprising caramelized sugar, Epsom salt, iodine tincture of 2.5% to 7%, pine tar, Arnica Montana 30x, lemon juice, and leather shavings and/or sandings,
      said adhesive composition being non-irritating to skin of said horse identified in said identifying step,
      said adhesive composition being sticky so as to remain in place on said bottom of said hoof after said applying step without a wrapping, and
      said applying step producing a coating of said adhesive composition adhering to said bottom of said hoof with an exposed surface,
         wherein said adhesive composition is prepared by the steps of:
         mixing sugar, said Arnica Montana 30x, said lemon juice, and water to produce a mixture;
         heating said mixture until said mixture caramelizes to form a caramel mixture;
         mixing said caramel mixture with said Epsom salt, said iodine tincture, said pine tar, and said leather shavings and/or sandings to form said adhesive composition; and
         cooling said adhesive composition.

2. The method of claim 1 further comprising the step of placing a cover of paper or cloth on said exposed surface of said adhesive composition, said placing step resulting in adherence of said cover to said adhesive composition without requiring a wrapping for said hoof.

3. The method of claim 1 wherein said identifying step identifies a horse having one or more of white line disease, seedy toe, abscesses, bacterial based hoof disease, and fungal based hoof disease.

4. The method of claim 1, wherein said applying step includes packing said adhesive composition into crevices in said bottom of said hoof.

5. A composition for treatment or relief of an infection, soreness, or inflammation of a hoof of a horse, comprising caramelized sugar, Epsom salt, iodine tincture of 2.5% to 7%, pine tar, Arnica Montana 30x, lemon juice, and leather shavings and/or sandings mixed together in the form of an adhesive composition which adheres to a bottom of a horse hoof without requiring a wrapping, and where said adhesive composition is non-irritating to skin of a horse,
   wherein said composition is prepared by the steps of:
   mixing sugar, said Arnica Montana 30x, said lemon juice, and water to produce a mixture;
   heating said mixture until said mixture caramelizes to form a caramel mixture;
   mixing said caramel mixture with said Epsom salt, said iodine tincture, said pine tar, and said leather shavings and/or sandings to form said adhesive composition; and
   cooling said adhesive composition.

6. The composition of claim 5 wherein said composition is packable into crevices in a bottom of a hoof of a horse.

* * * * *